United States Patent
Elokdah et al.

(10) Patent No.: US 6,288,100 B1
(45) Date of Patent: Sep. 11, 2001

(54) BENZIMIDAZOLE DERIVATIVES

(75) Inventors: Hassan M. Elokdah, Fairless Hills, PA (US); Sie-Yearl Chai, Lawrenceville, NJ (US); Theodore S. Sulkowski, Wayne, PA (US)

(73) Assignee: American Home Products Corporation, Madison, NJ (US)

( * ) Notice: Subject to any disclaimer, the term of this patent is extended or adjusted under 35 U.S.C. 154(b) by 0 days.

(21) Appl. No.: 08/468,482

(22) Filed: Jun. 6, 1995

(51) Int. Cl.[7] ............... A61K 31/415; C07D 235/26; C07D 235/22; C07D 235/12
(52) U.S. Cl. ................................. 514/394; 548/310.1
(58) Field of Search ................... 548/310.1; 514/394

(56) References Cited

U.S. PATENT DOCUMENTS

| | | |
|---|---|---|
| 4,814,329 | 3/1989 | Harsanyi et al. . |
| 4,859,684 * | 8/1989 | Raeymaekers et al. ............. 514/314 |
| 5,026,705 | 6/1991 | Prucher et al. . |
| 5,200,422 | 4/1993 | Olesen et al. . |
| 5,376,665 | 12/1994 | Miyata et al. . |
| 5,387,600 | 2/1995 | Aikawa et al. . |

FOREIGN PATENT DOCUMENTS 4212748   10/1993  (DE) .

OTHER PUBLICATIONS

Gevaert Photo–Producten N.Y., "Trimethine dyes, etc" CA 63:5797 (6) (1965).*
Venkataratnam, et al, "Studies on formation, etc" Ind. J of Chem, 29 B (1990) pp. 488–490.*
Beilstein Reference (50) 5–24 BRN # 811699.*

* cited by examiner

Primary Examiner—Patricia L. Morris
(74) Attorney, Agent, or Firm—Steven R. Eck

(57) ABSTRACT

Disclosed herein are compounds of formula I or II:

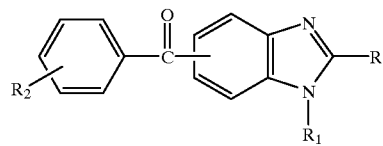

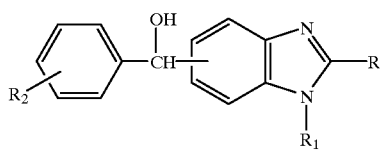

wherein

R is alkyl phenyl or substituted phenyl;

$R_2$ is hydrogen, halogen, alkoxy or alkyl;

$R_1$ is hydrogen, alkyl, aryl, arylalkyl, or substituted benzyl;

or a pharmaceutically acceptable salt thereof, which are useful as inhibitors of smooth muscle cell proliferation.

16 Claims, No Drawings

BENZIMIDAZOLE DERIVATIVES

BACKGROUND OF INVENTION

Proliferation and directed migration of vascular smooth muscle cells are important vascular occlusive components in such processes as hypertension-induced vascular remodeling, vascular restenosis, and atherosclerosis (Gibbons, G. H.; Dzau, V. J.; NEJM, 1994; 330: 1431). The overall disease process is referred to as hyperproliferative vascular disease based on the etiology of the disease process. Vascular occlusion is preceded by stenosis resulting from intimal smooth muscle cell hyperplasia (Clowes, A. W.; Reidy, M. A.; J. Vasc. Surg., 1991, 13: 885). The underlying cause of intimal smooth muscle cell hyperplasia is vascular smooth muscle cell injury leading to disruption of the endothelium and extracellular matrix (Schwartz, S. M., Human Pathology, 1987; 18: 240; Fingerle, J., Arteriosclerosis, 1990; 10: 1082). Normally, the cells of the arterial wall are under close negative control and in a low basal proliferating state or in a quiescent non-proliferating state. Following vascular injury, the release of growth factors and cytokines result in smooth muscle cell proliferation and migration (Fagin, J. A.; Forrester, J. S., Trends in Cardiovascular Med., 1992; 2; 90.; Shiratani, M.; Yui, Y.; Kawai, C., Endothelium, 1993; 1: 5).

Vascular injury leading to intimal hyperplasia can be induced immunologically or by invasive cardiovascular procedures. Atherosclerosis is a common form of biologically mediated vascular injury progressing to stenosis. Abnormal proliferation of vascular smooth muscle cells is a feature of atherosclerotic plaques responsible for obstructive neo-intimal lesions at the site of intimal damage (Ross, R., Nature, 1993: 362; 801; Cascells, W., Circulation, 1992; 86: 723). Mechanical injury leading to intimal hyperplasia can occur following angioplasty procedures, organ transplant surgery and other vascular invasive procedures that disrupt vascular integrity (Clowes, A. W.; Reidy, M. A., J. Vasc. Surg., 1991; 13: 885; Isik, F. F.; McDonald, T. O.; Ferguson, M.; Yanaka, E., Am. J. Pathol., 1992; 141: 1139).

Percutaneous transluminal coronary angioplasty has achieved wide acceptance for the treatment of coronary artery stenosis. In this procedure the endothelium is damaged and exposed to a variety of chemoattractants and mitogens which are either blood-borne or are released at the site of injury. Among these agents, platelet-derived growth factor (PDGF) is thought to play a significant role in the process of smooth muscle cell proliferation and chemotaxis (Reidy, M. A.; Fingerle, J.; Lindner, V.; Circulation, 1993: 86 (suppl III): III-43.; Ferns, G. A. A.; Raines, E. W.; Sprugel, K. H.; Montani, A. S.; Reidy, M. A.; Ross, R.; Science, 1991; 253: 1129.; Jawien, A., et al., J. Clin. Invest., 1992; 89: 507; Nabel, E. G., et al., J. Clin. Invest., 1993; 91: 1822). Within 3 to 6 months after angioplasty, a significant reduction in blood flow occurs in approximately 30–40% of patients as a result of restenosis caused by response to vascular injury during this procedure. These patients then require a second interventional procedure (Pepine, C., Circulation, 1990; 81: 1753.; Hardoff, R. J., J. Am. Coll. Cardiol., 1990; 15: 1486). Accordingly, agents that limit the restenosis process are of significant benefit. Agents that inhibit vascular smooth muscle cell proliferation, particularly PDGF-stimulated proliferation, are useful in the treatment of vascular hyperproliferative disorders (Molloy, C. J., Drug Dev. Res., 1993; 29: 148.; Newby, A. C.; George, S. J., Cardiovasc. Res., 1993; 27: 1173).

DE 4, 129, 603 discloses fused heterocyclic compounds (benzimidazoles) as inhibitors of collagen-induced platelet aggregation and fibrinogen, that may also be useful in the "treatment of transluminal angioplasty". U.S. Pat. No. 5,387,600 discloses 2-thio substituted benzimidazoles for the treatment of atherosclerosis. U.S. Pat. No. 5,026,705 discloses 2-styryl benzimidazolyl pyridazinones as positive inotropic agents useful in the treatment of congestive heart failure.

U.S. Pat. No. 5,200,422 discloses a family of 1-(substituted phenyl or naphthyl)-2H -benzimidazole-2-ones as potassium channel openers. U.S. Pat. No. 4,814,329 discloses 5-substituted-2-thiono or substituted-thio benzimidazole derivatives for treatment of hyperlipoproteinemic diseases and inhibition of atherosclerosis and thrombus formation. U.S. Pat. No. 5,376,665 discloses a group of 4-(benzimidazol -2-yl and benzthiazol -2-yl)-carbamoyl or sulfamoyl-benzyl phosphonate derivatives for the treatment of diabetes and hyperlipidemia.

DESCRIPTION OF THE INVENTION

In accordance with this invention, there is provided a group of benzoyl benzimidazoles (formula I) and reduction products thereof (formula II) as well as pharmaceutical compositions containing those compounds and the method of using the compounds in the treatment of conditions involving excessive smooth muscle cell proliferation such as restenosis, as follows:

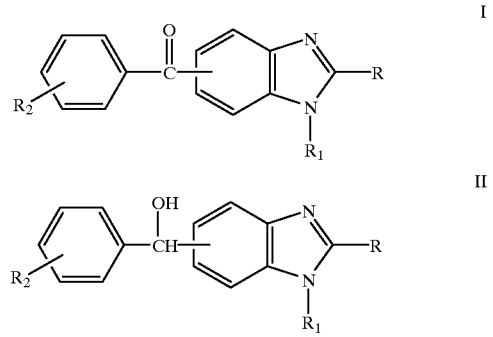

wherein R is alkyl of 1 to 6 carbon atoms, phenyl or phenyl substituted with halogen, hydroxyl, alkoxy of 1 to 6 carbon atoms, trifluoromethyl or alkyl of 1 to 6 carbon atoms; $R_2$ is hydrogen, halogen, alkoxy of 1 to 6 carbon atoms or alkyl of 1 to 6 carbon atoms; $R_1$ is hydrogen, alkyl of 1 to 6 carbon atoms, aryl of 6 to 10 carbon atoms, arylalkyl of 7 to 12 carbon atoms, or benzyl substituted with halogen, carboxyl, alkoxycarbonyl of 2 to 6 carbon atoms or aryloxycarbonyl of 7 to 12 carbon atoms, or a pharmaceutically acceptable salt thereof.

The compounds of this invention are prepared according to the general sequence of reactions outlined in the following scheme:

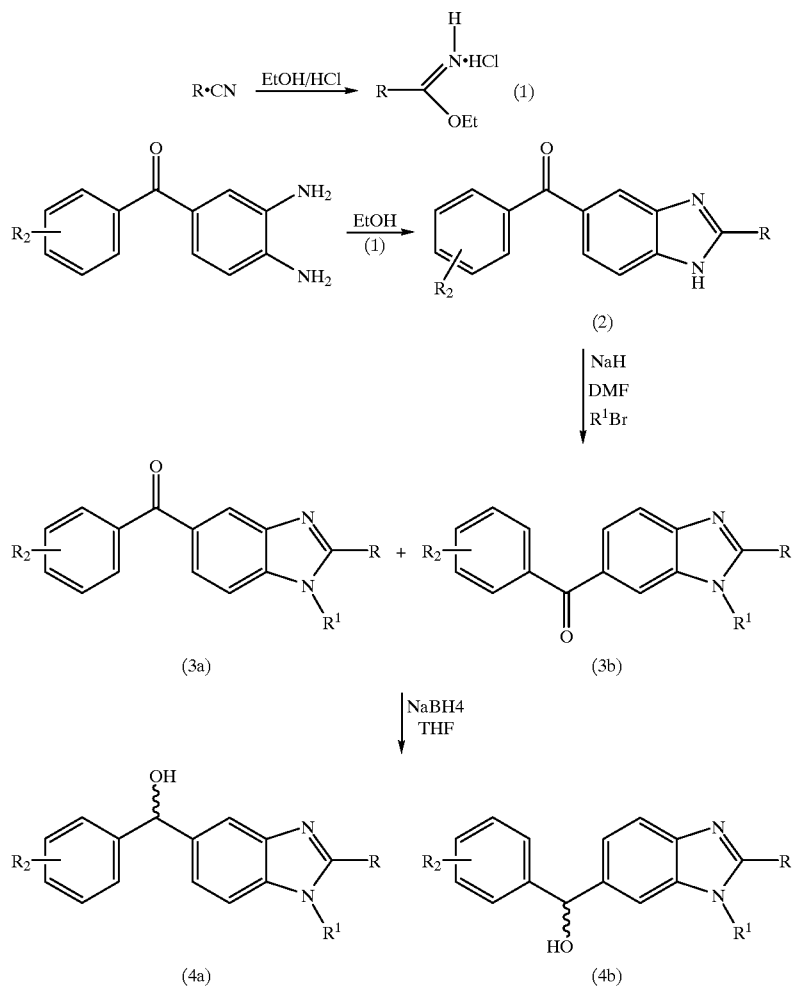

The iminoether hydrochloride (1) is prepared by reacting an appropriate nitrile with an alcohol and hydrogen chloride at around 0° C. Reaction of (1) and a 3,4-diaminobenzophenone in refluxing ethanol affords the corresponding benzoyl benzimidazole (2) substituted in the 2-position. Alkylation of (2) with an alkyl, aryl or arylalkyl halide in dimethyl formamide using sodium hydride as base affords the regioisomers (3a, 3b). The isomers can be separated by recrystallization and chromatography. The benzoylbenzimidazoles further can be reduced with sodium borohydride in ethanol to obtain the corresponding alcohols (4a, 4b).

The pharmaceutically acceptable acid addition salts are those derived from such organic and inorganic acids as: acetic, lactic, citric, fumaric, tartaric, succinic, maleic, malonic, hydrochloric, hydrobromic, phosphoric, nitric, sulfuric, methanesulfonic, methylbenzene sulfonic, and similarly known acceptable acids. With those compounds possessing an acidic substituent such as the carboxylic acids, the pharmaceutically acceptable salts include the alkali metal salts (sodium or potassium), the alkaline earth metal salts (calcium or magnesium) and ammonium salts.

This invention includes pharmaceutical compositions comprised of the benzimidazoles of the invention either alone or in combination with excipients (i.e. pharmaceutically acceptable materials with no pharmacological effect). Such compositions are useful in treating diseases which are characterized by excessive smooth muscle cell proliferation most frequently arising from vascular reconstructive surgery and transplantation, for example, balloon angioplasty, vascular graft surgery, coronary artery bypass surgery, and heart transplantation. Other disease states in which there is unwanted vascular proliferation include hypertension, asthma, and congestive heart failure. The compounds of this invention are thus useful for treating these diseases and states.

The compounds of this invention may be administered systemically, for example by intravenous injection, typically ranging from 0.1 to 10 mg/kg/h over 5–30 days, by subcutaneous injection at lower dose or by oral administration at higher dose than intravenous injection. Localized delivery of the compounds of this invention may also be achieved by transmembrane, transdermal or other topical administrative routes using appropriate continuous release devices such as a supporting matrix, where applicable. The compositions of the invention may be formulated with conventional excipients, such as a filler, a disintegrating agent, a binder, a lubricant, a flavoring agent and the like. These are formulated in a conventional manner.

The compounds may be administered neat or with a solid or liquid pharmaceutical carrier to a patient in need of such treatment. Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form. Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific patient suffering from a disease involving smooth muscle cell proliferation must be subjectively determined by the attending physician. The variables involved include the specific disease state and the size, age and response pattern of the patient.

The ability of the compounds of the present invention to inhibit smooth muscle cell proliferation was established using isolated porcine aortic smooth muscle cells in a modification of the procedure of Castellot et al. J. Biol. Chem 257(19) 11256 (1982), as follows:

Fresh porcine aortas, scrupulously cleansed of fatty tissue, are rinsed in sterile phosphate-buffered saline with 2% antibiotic-antimycotic (100x) liquid (10,000 units of penicillin (base), 10,000 $\mu$g of streptomycin (base), and 25 $\mu$g of amphotericin B/mL utilizing penicillin G (sodium salt), streptomycin sulfate, and amphotericin B as Fungizone® in 0.85% saline, available from Gibco Laboratories, Grand Island Biological Co., Grand Island, N.Y.). The tissue is then digested in 10–15 mL of an enzyme solution containing collagenase type I, 165 U/mL; elastase type III, 15 U/mL; BSA, 2 mg/mL; and soybean trypsin inhibitor, 0.375 mg/mL, followed by incubation at 37° C. under 5% $CO_2$ atmosphere for 10 to 15 minutes. After this treatment, the outer surface adventitia is removed by peeling with a forceps. The aorta is then longitudinally cut and laid open and the endothelial layer is removed by scraping.

The medial layer of cells is rinsed in the enzyme solution, and placed in a new 100 mm dish with 10 mL of enzyme solution. The medial layer of cells is minced using a fine pair of scissors and digested for 2–3 hours at 37° C. in 30 mL of fresh enzyme solution. After digestion, the medial tissue is homogenized using a sterile Pasteur pipette with a fire polished tip or an Eppendorf pipetter with a 200–1000 $\mu$L sterile pipette tip. The suspension is then centrifuged for 10 minutes at 8000 rpm and the pellet is suspended in 4–6 mL of fresh enzyme solution and plated onto 4–6 100 mm flasks with vented caps. The cells are then allowed to grow to confluence and split using 0.25% trypsin. The cells are evaluated for purity and overall quality using antibody to SMC actin.

The cells are assayed in early passage (generally passage 3–7) at sub-confluent conditions. Cultures are grown in 16 mm (24 well) multi-well culture dishes in media 199 supplemented with 10% fetal bovine serum and 2% antibiotic/antimycotic. At subconfluence, the cells are placed in a defined serum free, lymphocyte medium (AIM-V; Gibco) for 24–48 hours prior to initiating the experimental protocoL The standard test procedure is initiated by addition of the test compound, $^3$H thymidine and serum or a specific growth factor to the serum deprived synchronized cells. Growth factor and serum stimulations are optimized for each cell type. The test compounds are added to each well at 50 fold dilution (20 $\mu$L/well) and the plates are incubated for 24–36 hours at 37° C. in 5% $CO_2$ atmosphere. Test compounds are dissolved in 50% ethanol and assayed at 1, 10, and 100 $\mu$M. As a control, RG 50872 (Bilder, G. A.; et al., Am. J. Cell Physiol., 1991; 260: C721) is routinely assayed under the conditions of each cell preparation at a concentration of 5 $\mu$M.

At the completion of the experiment, the plates are placed on ice, washed three times with ice cold PBS and incubated in ice cold 10% trichloroacetic acid (TCA) for 30 minutes to remove acid soluble proteins. Each solution is transferred to a scintillation vial containing 0.4N HCl (500 $\mu$L/vial to neutralize NaOH) and each well is rinsed two times with water (500 $\mu$L) for a total volume of 2 mL/vial.

Data is quantitated by subjecting the vials to a scintillation counter, in triplicate, for both control and experimental samples. Control (100%) data is obtained from maximally stimulated cells, as the result of growth factor or serum stimulation. Experimental data is obtained from cells maximally stimulated with growth factor or serum and treated with a test compound. (The platelet-derived growth factor used in the assay was human recombinant PDGF-AB purchased from Upstate Biotechnology Inc., Lake Placid, N.Y.). Data is expressed as a percent of control from which $IC_{50}$s are determined.

To distinguish cytotoxicity from the ability of a compound to prevent proliferation, the test compounds were examined using a commercial modification of the MTT assay. Briefly, cells were grown in 24 well plates to 70–80% confluency. The cells were serum deprived for 24–48 hours prior to initiation of the experimental protocol. To insure that the MTT assay monitored toxicity rather than proliferation, the cells were incubated with 50 mM test compound in fresh medium without serum for 24 hours at 37° C. in a humidified $CO_2$ incubator. Upon completion of the compound treatment, MTT indicator dye was added for 4 hours at 37° C. Cells were then solubilized and aliquots from each well were transferred to a 96-well plate for analysis. Absorbance at 570 nm wavelength with a reference wavelength of 630 nm was recorded using an ELISA plate reader. Results are reported as percent viable using no drug (100% viable) and pre-solubilization (0% viable) standards.

The compounds of the present invention are effective inhibitors of smooth muscle cell proliferation as shown by the data presented in Table I.

TABLE I

| Compound of Example Number | Porcine Smooth Muscle Cell Antiproliferation $IC_{50}$ or % Inhibition at x Concentration | | Cytotoxicity % Viable Cells |
|---|---|---|---|
| | Serum | PDGF | |
| 1 | 39.4%/20 μM | 12.9 μM | 80 |
| 2 | 1.04 μM | 1.17 μM | 100 |
| 3 | 1.58 μM | 1.23 μM | 100 |
| 4 | 61.8%/20 μM | 0 | 100 |
| 5 | 41%/20 μM | 15.9 μM | 78 |
| 6 | 45.9%/20 μM | 11.2 μM | 85.5 |
| 7 | 36%/10 μM | 17.6 μM | 85 |
| 8 | 90%/20 μM | 0.096–0.465 μM | 100 |
| 9 | 8.03–11.42 μM | 3.74–4.14 μM | 100 |
| 10 | 13.5 μM | 0.762 μM | 100 |
| 11 | 1.82 μM | 7.7 μM | 100 |
| 12 | 7.74 μM | 0.081–0.140 μM | 100 |

The following examples are presented by way of illustration rather than limitation for representative compounds of the invention and methods for their production.

EXAMPLE 1

Step 1

Ethyl butyrimidate hydrochloride

A solution of butyronitrile (34.5 g; 0.5 mol) in ethanol (25 g; 0.54 mol) was cooled in an ice bath. The cold solution was then saturated with hydrogen chloride gas. The reaction mixture was refrigerated for 18 hours. The excess ethanol was evaporated under vacuum. The residual oil was then treated with a small amount of diethyl ether. Collection of the colorless solid provided the title compound (23 g, 30% yield) which was used in the reaction described in step 2 of this example. $^1$H-NMR (DMSO-$d_6$; 200 MHz): δ12.22 (br s, 1H), 11.33 (br s, 1H), 4.46 (q, 2H), 2.62 (t, 2H), 1.65 (m, 2H), 1.32 (t, 3H), and 0.92 ppm (t, 3H).

Step 2

Phenyl-(2-propyl-1H-benzoimidazol-5-yl)-methanone

A mixture of 3,4 diaminobenzophenone (21.2 g; 0.1 mol) and ethyl butyrimidate hydrochloride (22.7 g; 0.15 mol) in ethanol (500 mL) was heated at reflux for a period of 6 hours. The mixture was stirred at ambient temperature for 18 hours. The solvent was evaporated and the residue was purified by flash chromatography on silica gel (EtOAc/Hexane; 1:1). Crystallization from ethyl acetate provided 12 g (45% yield) of the title compound as an off-white solid, m.p. 131–132° C. Anal. Calcd. for $C_{17}H_{16}N_2O$: C, 77.25; H, 6.10; N, 10.60. Found: C, 77.20; H, 6.06; N, 10.72. Mass spectrum (EI; M$^+$) m/z 264. $^1$H-NMR (DMSO-$d_6$; 400 MHz) δ12.56 (br s, 1H), 7.84 (s, 1H), 7.73 (m, 2H), 7.65 (m, 1H), 7.60 (s, 2H), 7.56 (t, 2H), 2.82 (t, 2H), 1.80 (m, 2H), and 0.95 ppm (t, 3H).

EXAMPLE 2

Step 1

4-(5-Benzoyl-2-propyl-benzoimidazol-1-ylmethyl)-benzoic acid methyl ester (A) and 4-(6-Benzoyl-2-propyl-benzoimidazol 1-ylmethyl)-benzoic acid methyl ester (B)

Phenyl-(2-propyl-1H-benzoimidazol-5-yl)methanone (12.1 g; 45.8 mmol) was dissolved in DMF (300 mL) under an atmosphere of nitrogen. Sodium hydride (60% dispersion in oil, 3.7 g; 92.0 mmol) was then added portionwise. The mixture was then stirred at ambient temperature for 0.5 hour. Methyl 4-bromomethyl benzoate (10.5 g; 45.8 mmol) was then added. The reaction mixture was stirred for a period of 4 hours, then water (50 mL) was added. The mixture was concentrated under vacuum. The residue was then subjected to flash chromatography on silica gel EtOAc/Hexane; 1:1) affording the tide compounds.

Compound (A) eluted first giving 8.3 g (44% yield) as a white solid, m.p. 115–117° C. Anal. Calcd. for $C_{26}H_{24}N_2O_3$: C, 75.71; H, 5.86; N, 6.79. Found: C, 75.77; H, 5.98; N, 6.61. Mass spectrum (PBEI; M$^+$) m/z 412. $^1$H-NMR (DMSO-$d_6$; 400 MHz): δ7.95 (t, 3H), 7.73 (d, 2H), 7.59–7.68 (m, 3H), 7.56 (t, 2H), 7.23 (d, 2H), 5.67 (s, 2H), 3.82 (s, 2H), 2.82 (t, 2H), 1.74 (m, 2H), and 0.92 ppm (t, 3 H). Assignment of the regiochemistry was based on $^1$H-NMR (NOE) experiments.

Compound (B) eluted next giving 3.8 g (20%) as a white solid, m.p. 142–144° C. Anal. Calcd. for $C_{26}H_{24}N_4O_3$: C, 75.71; H, 5.86; N, 6.79. Found: C, 75.72; H, 6.00; N, 6.63. Mass spectrum (PBEI; M$^+$) m/z 412. $^1$H-NMR (DMSO-$d_6$; 400 MHz): δ7.92 (d, 2H), 7.82 (s, 1H), 7.73 (d, 1H), 7.58–7.64 (m, 4H), 7.48 (t, 2H), 7.20 (d, 2H), 5.68 (s, 2H), 3.83 (s, 2H), 2.87 (t, 2H), 1.77 (m, 2H), AND 0.94 PPM (T, 3H). Assignment of the regiochemistry was based on $^1$H-NMR (NOE) experiments.

Step 2

4-(5-Benzoyl-2-propyl-benzoimidazol-1-ylmethyl)-benzoic acid ethyl ester 4-(5-Benzoyl-2-propyl-benzoimidazol-1-ylmethyl)-benzoic acid methyl ester (2.0 g) was heated to reflux in ethanolic hydrogen chloride (100 mL) for a period of 24 hours. The solvent was evaporated. The residue was dissolved in fresh ethanol (100 mL). The resulting solution was decolorized with carbon. The mixture was filtered and evaporated. The residue was dissolved in ethyl acetate and washed with saturated sodium bicarbonate solution, then with water. The organic phase was evaporated. The residue was crystallized from EtOAc/Hexane to give 1.2 g (57% yield) of the title compound as a white solid, m.p. 126–128° C. Anal. Calcd. for $C_{27}H_{26}N_2O_3$: C, 76.03; H, 6.14; N, 6.57. Found: C, 76.04; H, 6.12; N, 6.56. Mass spectrum (EI; M$^+$) m/z 426. $^1$H-NMR (DMSO-$d_6$; 400 MHz): δ7.95 (s, 1H), 7.92 (d, 2H), 7.73 (d, 2H), 7.62–7.68 (m, 3H), 7.53–7.59 (m, 2H), 7.22 (d, 2H), 5.67 (s, 2H), 4.28 (q, 2H), 2.82 (t, 2H), 1.74 (m, 2H), 1.28 (t, 3H), and 0.92 ppm (t, 3H).

EXAMPLE 3

4-(6-Benzoyl-2-propyl-benzoimidazol-1-ylmethyl)-benzoic acid ethyl ester

The title compound was prepared by the procedure described in step 2 of example 2 using 1.5 g of 4-(6-

Benzoyl-2-propyl-benzoimidazol-1-ylmethyl)-benzoic acid methyl ester. Crystallization from EtOAc/Hexane afforded the title compound (0.9 g, 57% yield) as a white solid, m.p. 124–126° C. Anal. Calcd. for $C_{27}H_{26}N_2O_3$: C, 76.03; H, 6.14; N, 6.57. Found: C, 75.94; H, 6.08; N, 6.54. Mass spectrum (EI; M$^+$) m/z 426. $^1$H-NMR (DMSO-d$_6$; 400 MHz): δ7.92 (d, 2H), 7.81 (s, 1H), 7.72 (d, 1H), 7.58–7.65 (m, 4H), 7.49 (t, 2H), 7.20 (d, 2H), 5.68 (s, 2H), 4.29 (q, 2H), 2.88 (t, 2H), 1.77 (m, 2H), 1.29 (t, 3H), and 0.94 ppm (t, 3H).

EXAMPLE 4

4-(6-Benzoyl-2-propyl-benzoimidazol-1-ylmethyl) benzoic acid

A solution of potassium hydroxide (1.0 g in 10 mL of water) was added to a solution of 4-(6-benzoyl-2-propyl-benzoimidazol-1-ylmethyl)-benzoic acid methyl ester (1.0 g) in methanol (25 mL). The mixture was heated at reflux for a period of 3 hours. The reaction mixture was cooled to ambient temperature. The methanol was evaporated under vacuum. The residue was diluted with water (30 mL), then extracted with ethyl acetate (24 mL). The aqueous phase was acidified with 1N HCl. The precipitated solid was collected and air dried to afford the tide compound (0.6 g, 63% yield) as a white solid m.p. 295–296° C. Anal. Calcd. for $C_{25}H_{22}N_2O_3$: C, 75.36; H, 5.57; N, 7.03. Found: C, 75.03; H, 5.65; N, 6.86. Mass spectrum (PBEI; M$^+$) mlz 398. $^1$H-NMR (DMSO-d$_6$; 400 MHz): δ13.0 (br s, 1H), 7.91 (d, 2H), 7.82 (s, 1H), 7.72 (d, 1H), 7.58–7.64 (m, 4H), 7.47 (t, 2H), 7.18 (d, 2H), 5.67 (s, 2H), 2.88 (t, 2H), 1.78 (m, 2H), and 0.94 ppm (t, 3H).

EXAMPLE 5

4-(5-Benzoyl-2-propyl-benzoimidazol-1-ylmethyl)-benzoic acid

The title compound was prepared by the procedure described in step 1 of example 4 using 1.0 g of 4-(5-benzoyl-2-propyl-benzoimidazol-1-ylmethyl)-benzoic acid methyl ester. The title compound was obtained (0.65 g, 67% yield) as a white solid, m.p. 125–128° C. Anal. Calcd. for $C_{25}H_{22}N_2O_3$: C, 75.36; H, 5.57; N, 7.03. Found: C, 74.96; H, 5.79; N, 6.72. Mass spectrum (PBCI$^+$; [M+H] m/z 399. $^1$H -NMR (DMSO-d$_6$; 400 MHz): δ12.96 (br s, 1H), 7.95 (s, 1H), 7.90 (d, 2H), 7.73 (dd, 2H), 7.60–7.68 (m, 3H), 7.56 (t, 2H), 7.20 (d, 2H), 5.67 (s, 2H), 2.83 (dd, 2H), 1.75 (m, 2H), and 0.93 ppm (t, 3H).

EXAMPLE 6

Step 1

4-[6-(Hydroxy-(phenyl)-methyl)-2- propyl -benzoimidazol-1-ylmethyl]-benzoic acid ethyl ester To a solution of 4-(6-benzoyl-2-propyl-benzoimidazol-1-ylmethyl)-benzoic acid ethyl ester (1.5 g; 3.5 mmol) in ethanol (50 mL) was added sodium borohydride (1.0 g; 29.4 mmol). After stirring at ambient temperature for 4 hours, acetone (20 mL) was added. The solvent was evaporated. The residue was dissolved in ethyl acetate and washed with water. The organic phase was evaporated to give the title compound (0.9 g, 60% yield) as a white solid which was used without further purification in step 2.

Step 2

4-[5-(Hydroxy-(phenyl)-methyl)-2-propyl -benzoimidazol-1-ylmethyl]-benzoic acid

A solution of potassium hydroxide (1.0 g in 10 mL of water) was added to a solution of 4-[6-(hydroxy-(phenyl)-methyl)-2-propyl-benzoimidazol-1-ylmethyl]-benzoic acid ethyl ester (0.5 g) in ethanol (40 mL). The mixture was heated at reflux for a period of 4 hours. The solvent was evaporated. The residue was dissolved in water and neutralized with 1N HCl. The solid was collected by filtration and dried to give the tide compound as a mono hydrate (0.3 g, 60% yield), m.p. 146–149° C. Anal. Calcd. for $C_{25}H_{24}N_2O_3 \cdot H_2O$ : C, 71.75; H, 6.26; N, 6.69. Found: C, 71.78; H, 5.86; N, 6.39. Mass spectrum (DCI$^+$[M+H]$^+$m/z 401. $^1$H-NMR (DMSO-d$_6$; 400 MHz): δ12.96 (br s, 1H), 7.89 (d, 2H), 7.50 (m, 2H), 7.31 (d, 2H), 7.23 (t, 2H), 7.16 (t, 4H), 5.86 (br s, 1H), 5.74 (s, 1H), 5.58 (s, 2H), 2.81 (t, 2H), 1.73 (m, 2H), and 0.91 (t, 3H).

EXAMPLE 7

Step 1

4-[5-(Hydroxy-(phenyl)-methyl)-2-propyl -benzoimidazol-1-ylmethyl]-benzoic acid ethyl ester The title compound was prepared by the procedure described in step 1 of example 6 using 1.5 g of 4-(5-benzoyl-2-propyl-benzoimidazol-1-ylmethyl)-benzoic acid ethyl ester. The title compound was obtained (1.0 g, 67% yield) and was used without further purification in step 2.

Step 2

4-[5-(Hydroxy-(phenyl)-methyl)-2-propyl-benzoimi dazol-1-ylmethyl]-benzoic acid hydrochloride A solution of potassium hydroxide (1.0 g in 10 mL of water) was added to a solution of 4-[5-(hydroxy-(phenyl)-methyl)-2-propyl-benzoimidazol-1-ylmethyl]-benzoic acid ethyl ester (0.5 g) in ethanol (30 mL). The mixture was heated at reflux for a period of 4 hours. The solvent was evaporated. The residue was dissolved in warm water (50 mL). The resulting solution was acidified with concentrated HCl. The precipitated solid was collected by filtration and dried to give the tide compound as the monohydrochloride, monohydrate(0.4 g, 75% yield) as a white solid, m.p. 209–212° C. Anal. Calcd. for $C_{25}H_{24}N_2O_3 \cdot HCl \cdot H_2O$: C, 66.00; H, 5.98; N, 6.16; Cl, 7.81. Found: C, 65.90; H, 5.82; N, 6.15; Cl, 8.20. Mass spectrum (EI; M$^+$) m/z 400. $^1$H -NMR (DMSO-d$_6$; 400 MHz) δ13.0 (br s, 1H), 7.90 (d, 2H), 7.82 (s, 1H), 7.64 (d, 1H), 7.47 (d, 1H), 7.39 (d, 2H), 7.28–7.34 (q, 4H), 7.19 (t 1H), 6.12 (br s, 1H), 5.89 (s, 1H), 5.81 (s, 2H), 3.14 (t, 2H), 1.77 (m, 2H), and 0.92 ppm (t, 3H).

EXAMPLE 8

[1-(3,4-Dichloro-benzyl)-2-propyl-1H-benzoimidazol-5-yl]-phenyl-methanone

A solution of phenyl-(2-propyl-1H-benzoimidazol-5-yl) methanone (5.28 g; 0.02 mol) in DMF (80 mL) was stirred under an atmosphere of nitrogen. Sodium hydride (60% dispersion in oil, 0.8 g; 0.02 mol) was added. The mixture was then stirred for 0.5 hour at ambient temperature. 3,4-dichlorobenzyl bromide (4.8 g; 0.02 mol) was then added in portions. The mixture was stirred at 80–90° C. for 3.5 hours, then at ambient temperature for 18 hours. The solvent was evaporated under vacuum. The residue was extracted with ethyl acetate (300 mL) and washed with water (2×200 mL). The organic phase was evaporated. Purification was achieved by flash chromatography on silica gel (EtOAc/Hexane; 1:9 to 1:3). Recrystallization from ethyl acetate affords the tide compound (4.2 g; 50% yield) as a white solid, m.p. 168–169° C. Anal. Calcd. for $C_{24}H_{20}Cl_2N_2O$: C, 68.09; H, 4.76; N, 6.62. Found: C, 67.70; H, 4.46; N, 6.49. Mass spectrum (DEI; M$^+$) m/z 422, 424, 426. $^1$H-NMR (DMSO -d$_6$; 400 MHz) δ7.94 (d, 1H), 7.73 (d, 2H), 7.64–7.72 (m, 3H), 7.59 (m, 1H), 7.56 (t, 2H), 7.47 (d, 1H), 6.98 (dd, 1H), 5.59 (s, 2H), 2.84 (t, 2H), 1.76 (m, 2H) and 0.94 ppm (t, 3H).

EXAMPLE 9

Step 1

Ethyl-(4-Hydroxy-3-methoxy)-benzoimidate hydrochloride

A solution of 4-hydroxy-3-methoxybenzonitrile (10 g, 67 mmol) in 60 mL of ethyl alcohol was cooled in an ice bath. The cold solution was then saturated with hydrogen chloride gas. The reaction mixture was kept refrigerated for 18 hours. The precipitate was collected by filtration. The colorless solid gave 7.2 g (47% yield) of the tide compound which was used in the next reaction, m.p. 151–154° C. $^1$H-NMR (DMSO-d$_6$; 200 MHz) δ11.78 (s, 1H), 10.9 (s,lH), 7.8 (s,lH), 7.6 (d, 1H), 6.98 (d, 1H), 4.5 (q, 2H), 3.8 (s, 3H), and 1.4 ppm (t, 3;H).

Step 2

[2-(4-Hydroxy-3-methoxy-phenyl)1H-benzoimidazol-5-yl]-phenyl-methanone

A mixture of 3,4-diaminobenzophenone (2.12 g; 10 mmol) and ethyl-(4 -hydroxy-3-methoxy)-benzoimidate hydrochloride (2.31 g; 10 mmol) in ethanol (70 mL) was stirred at ambient temperature for 18 hours. Yellow solid formed was separated by filtration. Recrystallization from ethanol gave 862 mg (26% yield) of the title compound as a creamy solid, hydrochloride, m.p. 261° C. dec. Anal. Calcd. for $C_{21}H_{16}N_2O_3$.HCl: C, 66.23 H, 4.50; N, 7.35. Found: C, 65.69; H, 4.37; N, 7.18. $^1$H-NMR (DMSO-d$_6$; 400 MHz) δ8.08 (s, 1H), 8.02 (s, 1H), 7.85–7.92 (m, 3H), 7.8 (d, 2H), 7.7 (t, 1H), 7.6 (t, 2H), 7.08 (d, 1H), 3.9 (s, 3H), 3.8 ppm (s, 1H).

EXAMPLE 10

Step 1

4-Hexyloxy-3-methoxybenzonitrile

To a suspension of sodium hydride, 60% dispersion in oil,(4.8 g; 0.11 mol) in 40 mL of DMF, a solution of 4-hydroxy-3-methoxy-benzonitrile (14.9 g; 0.1 mol) in DMF (40 mL) was added dropwise over 10 minutes. After addition, the reaction mixture was stirred at ambient temperature for 30 minutes, then bromohexane (16.5 g; 0.1 mol) in DMF (20 mL) was added. The reaction mixture was stirred at ambient temperature for 18 hours. The DMF containing reaction mixture was concentrated to a residue, and H$_2$O (100 mL) was added to the residue. The solid was collected by filtration to obtain 8.2 g (35% yield) of the tide compound as white solid. $^1$H-NMR (DMSO-d$_6$; 200 MHz) δ7.45 (s, 1H), 7.42 (s, 1H), 7.1 (d, 1H), 4.0 (t, 2H), 3.8 (s, 3H), 1.6–1.8 (m, 2H), 1.2–1.5 (m, 8H), and 0.9 ppm (t, 3H).

Step 2

Methyl-(4-Hexyloxy-3-methoxy)-benzoimidate hydrochloride

The title compound was prepared in 60% yield (3.1 g)by the procedure of step 1 of Example 9 using 4-hexyloxy-3-methoxybenzonitrile (4.0 g; 17 mmol) and methanol. $^1$H-NMR (DMSO-d$_6$; 200MHz) δ11.6 (s, 1H), 7.8–7.7 (d, 2H), 7.2 (d, 1H), 4.13 (s, 3H), 4.1 (t, 2H), 3.82 (s, 3H), 1.6–1.8 (m, 2H), 1.2–1.5 (m, 8H), 0.85 ppm (t, 3H).

Step 3

[2-(4-Hexyloxy-3-methoxy-phenyl)-1H benzoimidazol-5-yl]phenyl-methanone

A mixture of 3,4-diaminobenzophenone (1.49 g; 6.6 mmol) and methyl-(4-hexyloxy-3-methoxy)-benzoimidate hydrochloride (2.0 g; 6.6 mmol) in methanol (50 mL) was stirred at ambient temperature for 72 hours. Precipitate formed was collected by filtration. The creamy solid gave 1.4 g (50% yield) of the title compound, m.p. 150–153° C. Anal. Calcd. for $C_{27}H_{28}N_2O_3$.: C, 75.68, H, 6.59; N, 6.54. Found: C, 75.67; H, 6.59; N, 6.54. Mass Spectrum: (EI; M$^+$) m/z 428. $^1$H-NMR (DMSO -d$_6$; 400 MHz) δ7.85–7.9 (d, 1H), 7.71–7.8 (m, 4H), 7.62–7.7 (dd,3H), 7.6 (t, 2H), 7.15 (d, 1H), 4.1 (t, 2H), 3.89 (s, 3H), 1.7–1.8 (m, 2H), 1.38–1.46 (m, 2H), 1.26–1.35 (m, 4H), 0.88 ppm (t, 3H).

EXAMPLE 11

Step 1

Methyl-(4-Trifluoromethoxy)-benzoimidate hydrochloride

The title compound was prepared in 59% yield (4.0 g) from 4-trifluoromethoxybenzonitrile (5.0 g; 26 mmol) and methanol (50 mL) using the procedure described in the step 1 of Example 9, m.p. 148–151° C.

Step 2

Phenyl- [2-(4-trifluoromethoxy-phenyl)-1H -benzoimidazol-5-yl]methanone

The title compound was prepared by the procedure described in step 3 of Example 10 using methyl-(4-trifluoromethoxy)- benzoimidate hydrochloride (2.0 g; 7.8 mmol). Recrystallization from methanol afforded 1.5 g (52%) of off-white solid, m.p. 215–217° C. Anal. Calcd. for $C_{21}H_{13}N_2O_2F_3$: C, 65.97; H, 3.43; N, 7.33; Found: C, 66.09; H, 3.28; N, 7.34. $^1$H-NMR (DMSO-d$_6$; 200MHz) δ13.5 (d, 1H), 8.3–8.4 (d, 2H), 7.9–8.1 (d, 1H), 7.7–7.9 (m, 5H), 7.5–7.6 ppm (m, 4H).

EXAMPLE 12

Step 1

Methyl-(3,4-Dimethoxyphenyl)-acetimidate hydrochloride

The title compound was prepared by the procedure described in step 1 of Example 9 using 3,4-dimethoxyphenylacetonitrile (10 g; 56 mmol) in methanol (150 mL). 7.8 g (54% yield) of the title compound was obtained and used in the next reaction.

Step 2

[2-(3,4-Dimethoxybenzyl)-1H-benzoimidazol-5-yl]-phenyl-methanone

A mixture of methyl-(3,4dimethoxyphenyl)-acetimidate hydrochloride (2.5 g; 10 mmol) and 2,3-diamiinobenzophenone (2.1 g; 10 mmol) in methanol (70 mL) was stirred at ambient temperature for 72 hours. The reaction mixture was concentrated to dryness, and H$_2$O was added. The solid (2.3 g) was subjected to flash chromatography on silica gel (CH$_2$Cl$_2$/MeOH; 9:1) to afford a gummy material. This was dissolved in diethyl ether, and Ether-HCl was added to obtain the title compound as a buff solid, hydrochloride, penta-hydrate (250 mg), m.p. 172–175° C. Anal. Calcd. for C$_{23}$H$_{20}$N$_2$O$_3$HCl.5H$_2$O: C, 66.97; H, 5.23; N, 6.79. Found: C, 67.11, H, 4.84; N, 6.77. Mass Spectrum: (EI; M$^+$) m/z 372. $^1$H-NMR (D)MSO-d$_6$; 400 MHz) δ8.0 (s, 1H) 7.84–7.9 (m, 2H), 7.68–7.77 (m, 3H), 7.55–7.61 (m, 2H), 7.2 (s, 1H), 6.93–7.01 (m, 2H), 4.42 (s, 2H), 3.79 (s, 3H), 3.77 ppm (s, 3H).

What is claimed is:

1. A compound of formula I or II:

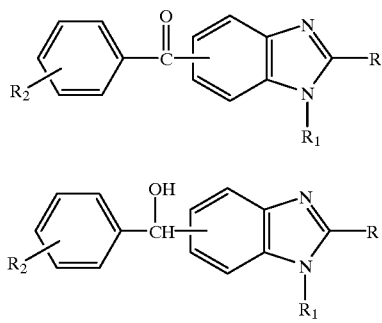

wherein

R is alkyl of 1 to 6 carbon atoms, substituted phenyl or substituted benzyl, in which the substituents are hydroxyl, alkoxy of 1 to 6 carbon atoms, trifluoromethoxy or alkyl of 1 to 6 carbon atoms;

R$_2$ is hydrogen;

R$_1$ is hydrogen, benzyl or benzyl substituted with halogen, carboxyl, alkoxycarbonyl of 2 to 6 carbon atoms or aryloxycarbonyl of 7 to 12 carbon atoms, or a pharmaceutically acceptable salt thereof.

2. A compound selected from the group consisting of phenyl-(2-propyl-1H-benzoimidazol-5-yl)-methanone,
4-(5-benzoyl-2-propyl-benzoimidazol-1-ylmethyl)-benzoic acid ethyl ester,
4-(6-benzoyl-2-propyl-benzoimidazol-1-ylmethyl)-benzoic acid ethyl ester,
4-(6-benzoyl-2-propyl-benzoimidazol-1-ylmethyl)benzoic acid,
4-(5-benzoyl-2-propyl-benzoimidazol-1-ylmethyl)-benzoic acid,
4-[5-(hydroxy-(phenyl)-methyl)-2-propyl-benzoimidazol-1-ylmethyl]-benzoic acid,
[1-(3,4-dichloro-benzyl)-2-propyl-1H-benzoimidazol-5yl] phenyl -methanone,
[2-(4-hydroxy-3-methoxy-phenyl)-1H-benzoimidazol-5-yl]-phenyl -methanone,
[2-(4hexyloxy-3-methoxy-phenyl)-1H-benzoimidazol-5-yl]-phenyl -methanone,
phenyl-[2-(4-trifluoromethoxy-phenyl)-1H-benzoimidazol-5-yl]-methanone, and
[2-(3,4-dimethoxybenzyl)-1H-benzoimidazol-5yl]-phenyl-methanone.

3. A pharmaceutical composition comprising a compound of formula I or II:

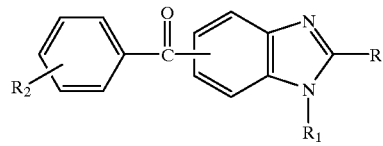

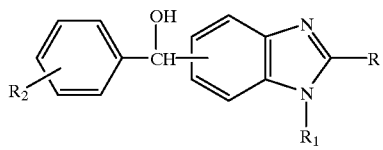

wherein

R is alkyl of 1 to 6 carbon atoms, phenyl, benzyl, or substituted phenyl or substituted benzyl, in which the substituents are halogen, hydroxyl, alkoxy of 1 to 6 carbon atoms, trifluoromethoxy or alkyl of 1 to 6 carbon atoms;

R$_2$ is hydrogen, halogen, alkoxy of 1 to 6 carbon atoms or alkyl of 1 to 6 carbon atoms;

R$_1$ is hydrogen, alkyl of 1 to 6 carbon atoms, aryl of 6 to 10 carbon atoms, arylalkyl of 7 to 12 carbon atoms, or benzyl substituted with halogen, carboxyl, alkoxycarbonyl of 2 to 6 carbon atoms or aryloxycarbonyl of 7 to 12 carbon atoms, or a pharmaceutically acceptable salt thereof, and a pharmaceutically acceptable carrier.

4. A method for treating diseases characterized by excessive smooth muscle cell proliferation in a mammal which comprises administering to that mammal, orally or parenterally, a smooth muscle proliferation inhibiting amount of a compound of formula I or II:

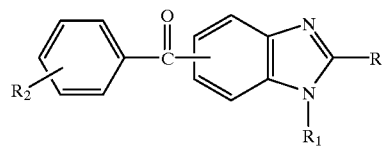

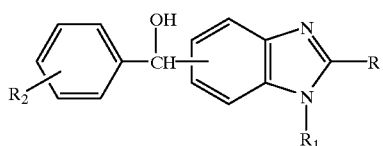

wherein

R is alkyl of 1 to 6 carbon atoms, phenyl or benzyl or substituted phenyl or substituted benzyl, in which the substituents are halogen, hydroxyl, alkoxy of 1 to 6 carbon atoms, trifluoromethoxy or alkyl of 1 to 6 carbon atoms;

R$_2$ is hydrogen, halogen, alkoxy of 1 to 6 carbon atoms or alkyl of 1 to 6 carbon atoms;

R$_1$ is hydrogen, alkyl of 1 to 6 carbon atoms, aryl of 6 to 10 carbon atoms, arylalkyl of 7 to 12 carbon atoms, or benzyl substituted with halogen, carboxyl, alkoxycarbonyl of 2 to 6 carbon atoms or aryloxycarbonyl of 7 to 12 carbon atoms, or a pharmaceutically acceptable salt thereof.

5. A method according to claim 4 wherein said smooth muscle cell proliferation manifests itself as restenosis following angioplasty.

6. The compound of claim 2 which is phenyl-(2-propyl-1H-benzoimidazol-5-yl)-methanone or a pharmaceutically acceptable salt thereof.

7. The compound of claim 2 which is 4-(5-benzoyl-2-propyl-benzoimidazol-1-ylmethyl)-benzoic acid ethyl ester or a pharmaceutically acceptable salt thereof.

8. The compound of claim 2 which is 4-(6-benzoyl-2-propyl-benzoimidazol-1-ylmethyl)-benzoic acid ethyl ester or a pharmaceutically acceptable salt thereof.

9. The compound of claim 2 which is 4-(6-benzoyl-2-propyl-benzoimidazol-1-ylmethyl)benzoic acid or a pharmaceutically acceptable salt thereof.

10. The compound of claim 2 which is 4-(5-benzoyl-2-propyl-benzoimidazol-1-ylmethyl)-benzoic acid or a pharmaceutically acceptable salt thereof.

11. The compound of claim 2 which is 4-[5-(hydroxy-(phenyl)-methyl)-2-propyl-benzoimidazol-1-ylmethyl]-benzoic acid or a pharmaceutically acceptable salt thereof.

12. The compound of claim 2 which is [1-(3,4-dichloro-benzyl)-2-propyl-1H-benzoimidazol-5yl]-phenyl-methanone or a pharmaceutically acceptable salt thereof.

13. The compound of claim 2 which is [2-(4-hydroxy-3-methoxy-phenyl)-1H-benzoimidazol-5-yl]-phenyl-methanone or a pharmaceutically acceptable salt thereof.

14. The compound of claim 2 which is [2-(4-hexyloxy-3-methoxy-phenyl)-1H-benzoimidazol-5-yl]-phenyl-methanone or a pharmaceutically acceptable salt thereof.

15. The compound of claim 2 which is phenyl-[2-(4trifluoromethoxy-phenyl)-1H-benzoimidazol-5-yl]-methanone or a pharmaceutically acceptable salt thereof.

16. The compound of claim 2 which is [2-(3,4-dimethoxybenzyl)-1H-benzoimidazol-5-yl]-phenyl-methanone or a pharmaceutically acceptable salt thereof.

* * * * *